US006335469B1

(12) United States Patent
Lukács et al.

(10) Patent No.: US 6,335,469 B1
(45) Date of Patent: Jan. 1, 2002

(54) HIGH PURITY (1R,2S,4R)-(-)-2-[(2'-{N,N-DIMETHYLAMINO}-ETHOXY)]-2-[PHENYL]-1,7,7-TRI-[METHYL]-BICYCLO[2.2.1] HEPTANE AND PHARMACEUTICALLY ACCEPTABLE ACID ADDITION SALTS THEREOF

(75) Inventors: Gyula Lukács; Gyula Simig; Tibor Mezei; Zoltán Budai; Márta Porcs-Makkay; György Krasznai; Kálmán Nagy; Györgyi Donáth Vereczkey; Tibor Szabó; Norbert Németh; János Szulágyi, all of Budapest (HU)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/569,046

(22) Filed: May 10, 2000

(30) Foreign Application Priority Data

May 11, 1999 (HU) .............................................. 99 01559

(51) Int. Cl.$^7$ ............................................. C07C 215/00
(52) U.S. Cl. ........................ 564/443; 564/305; 564/338; 514/650; 514/646
(58) Field of Search ................ 564/305, 338, 564/443, 409; 514/650, 646

(56) References Cited

U.S. PATENT DOCUMENTS 4,342,762 A    8/1982    Budai et al.

FOREIGN PATENT DOCUMENTS

| EP | 0 694 299 | 1/1996 |
| GB | 2 065 122 | 6/1981 |
| HU | 179 164 | 9/1986 |
| HU | 212 574 | 8/1996 |
| WO | WO 98/17230 | 4/1998 |
| WO | WO 00/50379 | 8/2000 |

OTHER PUBLICATIONS

Chemical Abstract, vol. 118, No. 23, 118: 234291c, XP–002156197 (1993).
Derwent Abstract of HU 212 574 Aug. 1996.
English translation of HU 212 574, Aug. 1996.

*Primary Examiner*—Samuel Barts
(74) *Attorney, Agent, or Firm*—Finnegan, Henderson, Farabow, Garrett & Dunner, L.L.P.

(57) ABSTRACT

The invention relates to high purity (1R,2S,4R)-(-)-2-[(2'-{N,N-dimethylamino}-ethoxy)]-2-[phenyl]-1,7,7-tri-[methyl]-bicyclo[2.2.1]heptane and pharmaceutically acceptable acid addition salts thereof containing not more than 0.2% of (1R,3S,4R)-3-[(2'-{N,N-dimethylamino}-ethyl)]-1,7,7-tri-[methyl]-bicyclo[2.2.1]heptane-2-one and/or of a pharmaceutically acceptable acid addition salt thereof.

Furthermore the invention is concerned with a process for the preparation of these compounds.

Moreover the invention relates to medicaments containing 1 or more of these compounds and their use.

17 Claims, No Drawings

HIGH PURITY (1R,2S,4R)-(-)-2-[(2'-{N,N-DIMETHYLAMINO}-ETHOXY)]-2-[PHENYL]-1,7,7-TRI-[METHYL]-BICYCLO[2.2.1] HEPTANE AND PHARMACEUTICALLY ACCEPTABLE ACID ADDITION SALTS THEREOF

The invention relates to high purity (1R,2S,4R)-(-)-2-[(2'-{N,N-dimethylamino}-ethoxy)]-2-[phenyl]-1,7,7-tri-[methyl]-bicyclo[2.2.1]heptane and pharmaceutically acceptable acid addition salts thereof and a process for the preparation of these compounds as well as medicaments containing 1 or more of these compounds and their use.

The 2-(E)-butenedioate (1:1) salt (fumarate) of (1R,2S,4R)-(-)-2-[(2'-{N,N-dimethylamino)-ethoxy)]-2-[phenyl]-1,7,7-tri-[methyl]-bicyclo[2.2.1]heptane of Formula

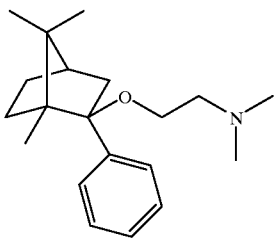

I is a known anxiolytic active principle having the INN "deramciclane fumarate".

The compound of Formula I falls under the general Formula I of Hungarian patent No. 179,164 but has not been actually and explicitly disclosed in this patent specification, nor the preparation thereof has been exemplified. According to Hungarian patent No. 179,164 the alkanol amine cycloalkyl ethers of its general Formula I are prepared by reacting (+)-1,7,7-tri-[methyl]-bicyclo[2.2.1]heptane-2-one, i. e. (+)-camphor of Formula

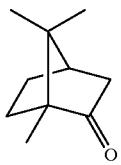

II with the corresponding organic metal compound, subjecting the adduct obtained to hydrolysis and introducing onto the hydroxy group of the product obtained the basic side chain by etherification. As organic metal compound a Grignard compound or an organic alkali metal compound, preferably lithium or sodium compound, is used.

The preparation of the compound of Formula I has been actually disclosed in Hungarian patent No. 212,574. The essence of this process is that purification of the product is carried out at a later stage of the synthesis. According to the process (+)-camphor of Formula II is subjected to Grignard reaction with phenyl magnesium bromide in diethyl ether to give (1R,2S,4R)-(-)-2-[phenyl]-1,7,7-tri-[methyl]-bicyclo[2.2.1]heptane-2-ol of Formula

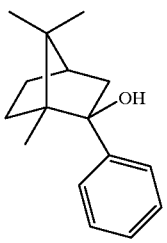

III with a yield of 28% (according to GC). The compound (1R,2S,4R)-(-)-2-[phenyl]-1,7,7-tri-[methyl]-bicyclo[2.2.1] heptane-2-ol of Formula III is in the reaction mixture and is not isolated. The complex is decomposed, the reaction mixture is converted without purification into the sodium salt by reaction with sodium amide or sodium hydride and the sodium salt obtained is reacted with anhydrous (2-{chloro}-ethyl)-dimethylamine in toluene as medium. The reaction mixture contains beside the base (1R,2S,4R)-(-)-2-[(2'-{N,N-dimethylamino}-ethoxy)]-2-[phenyl]-1,7,7-tri-[methyl]-bicyclo[2.2]heptane of Formula I (being present in an amount of 20 to 30%) a considerable amount of impurities and starting materials, e.g. unreacted (+)-camphor of Formula II, (1R,2S,4R)-(-)-2-[phenyl]-1,7,7-tri-[methyl]-bicyclo[2.2.1]heptane-2-ol, 1,7,7-tri-[methyl]-bicyclo[2.2.1]heptane-2-ol and biphenyl, triphenyl impurities, etc. The base (1R,2S,4R)-(-)-2-[(2'-{N,N-dimethylamino}-ethoxy)]-2-[phenyl]-1,7,7-tri-[methyl]-bicyclo[2.2.1]heptane of Formula I is separated from said contaminations by extraction with aqueous tartaric acid, whereupon the base is set free and the fumarate salt is formed. The total amount of unreacted (+)-camphor of Formula II and (1R,2S,4R)-(-)-2-[phenyl]-1,7,7-tri-[methyl]-bicyclo[2.2.1]heptane-2-ol of Formula III remains in the organic phase of the tartaric acid extraction step, which can be re-used in the Grignard reaction after removing the solvent and water (i.e. it can be re-circulated into the process). Thus the (+)-camphor used can be more efficiently utilized; without re-circulation only about 16% by weight of the (+)-camphor used can be utilized, while in case of a one-fold and three-fold re-circulation this value is increased to 22% by weight and 25% by weight, respectively.

It is very important and is to be emphasized that a considerable part of (+)-camphor of Formula II used in the Grignard reaction does not react and this starting material cannot be technically removed from the desired product because of the physical properties of (+)-camphor and the lability of the compound (1R,2S,4R)-(-)-2-[phenyl]-1,7,7-tri-[methyl]-bicyclo[2.2.1]heptane-2-ol of Formula III formed since compound (1R,2S,4R)-(-)-2-[phenyl]-1,7,7-tri-[methyl]-bicyclo[2.2.1]heptane-2-ol of Formula III is susceptible to decomposition. For this reason according to the process disclosed in Hungarian patent No. 212,574 the alkylation step always takes place in the presence of (+)-camphor of Formula II.

The aforesaid gives rise to the drawbacks of the process disclosed in Hungarian patent No. 212,574. The alkali hydrides and amides used in the first step of the alkylation reaction form salts not only with the alcohol (1R,2S,4R)-(-)-2-[phenyl]-1,7,7-tri-[methyl]-bicyclo[2.2.1]heptane-2-ol of Formula III but also with (+)-camphor of Formula II and other compounds containing an active hydrogen atom being present in the reaction mixture. For this reason beside the desired compound (1R,2S,4R)-(-)-2-[(2'-{N,N-dimethylamino}-ethoxy)3-2-[phenyl]-1,7,7-tri-[methyl]- bicyclo[2.2.1]heptane of Formula I further alkylated derivatives formed, e.g. from unreacted (+)-camphor, are obtained and the desired compound (1R,2S,4R)-(−)-2-[(2'-{N,N-dimethylamino}-ethoxy)]-2-[phenyl]-1,7,7-tri-methyl]-bicyclo[2.2.1]heptane of Formula I is to be recovered from a mixture containing such impurities and also unreacted compounds (+)-camphor and (1R,2S,4R)-(−)-2-[phenyl]-1,7,7-tri-[methyl]-bicyclo[2.2.1]heptane-2-ol of Formulae II and III. The crude compound (1R,2S,4R)-(−)-2-[(2'-{N,N-dimethylamino}-ethoxy)]-2-[phenyl]-1,7,7-tri-[methyl]-bicyclo[2.2.1]heptane of Formula I can only be purified, though incompletely, by means of recrystallization from dimethyl formamide. However, with the aid of said recrystallization only non-basic contaminations can be completely removed, which do not form salts.

A further disadvantage of recrystallization from dimethyl formamide is that the traces of the solvent cannot be removed from the desired pharmaceutical active principle to the required extent. In this regard it is to be noted that according to ICH (International analytical requirements accepted by the US, Japan and the EU) the limit of dimethyl formamide is 880 ppm (0.088% by weight). The reason for that the dimethyl formamide cannot be removed to such an extent but a greater amount of it remains in the product is the high boiling point of dimethyl formamide, on the one hand, and the sensitivity of (1R,2S,4R)-(−)-2-[(2'-{N,N-dimethylamino}-ethoxy)]-2-[phenyl]-1,7,7-tri-[methyl]-bicyclo[2.2.1]heptane of Formula I to thermal treatment, on the other hand.

It has been found that in case of the alkylation reaction of (1R,2S,4R)-( )-)-2-[phenyl]-1,7,7-tri-[methyl]-bicyclo[2.2.1]heptane-2-ol of Formula III carried out with (2-{chloro}-ethyl)-dimethylamine (+)-camphor of Formula II being always present gives rise to the formation of considerable amounts of by-products, e.g. (1R,3S,4R)-3-[(2'-(N,N-dimethylamino}-ethyl)]-1,7,7-tri-[methyl]-bicyclo[2.2.1]heptane-2-one of Formula

V

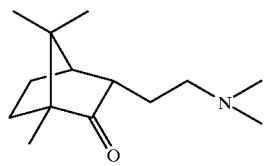

The by-product (1R,3S,4R)-3-[(2'-{N,N-dimethylamino}-ethyl)]-1,7,7-tri-[methyl]-bicyclo[2.2.1] heptane-2-one of Formula V is formed as follows: under the conditions used in the etherification reaction (+)-camphor of Formula II forms an alkali salt in position 3 which in turn reacts with the (2-{chloro}-ethyl)-dimethylamine used as alkylating agent to yield the compound of Formula V. The amount of the by-product of Formula V may be as high as 1 to 10% by weight. The solubility of the fumarate 2-(E)-butenedioate (1:1) of the compound of (1R,3S,4R)-3-[(2'-{N,N-dimethylamino}-ethyl)]-1,7,7-tri-[methyl]-bicyclo [2.2.1]heptane-2-one of Formula V is approximately identical with that of the fumarate of the desired compound (1R,2S,4R)-(−)-2-[(2'-{N,N-dimethylamino}-ethoxy)]-2-[phenyl]-1,7,7-tri-[methyl]-bicyclo[2.2.1]heptane of Formula I and therefore crystallizes together with the fumarate of the compound (1R,2S,4R)-(−)-2-[(2'-{N,N-dimethylamino}-ethoxy)]-2-[phenyl]-1,7,7-tri-[methyl]-bicyclo[2.2.1]heptane of Formula I and contaminates the desired end product. If the etherification is carried out in toluene, as described in Hungarian patent No. 212,574, the product obtained after salt formation in ethanol contains considerable amounts of the impurity (1R,3S,4R)-3-[(2'-{N,N-dimethylamino}-ethyl)]-1,7,7-tri-[methyl]-bicyclo[2.2.1] heptane-2-one of Formula V.

The salt is a highly unsoluble compound and can be recrystallized only from dimethyl formamide. However, recrystallization from dimethyl formamide fails to provide a compound (1R,2S,4R)-(−)-2-[(2'-{N,N-dimethylamino}-ethoxy)]-2-[phenyl]-1,7,7-tri-[methyl]-bicyclo[2.2.1] heptane of Formula I in a purity required by the Pharmacopoeias for the following reasons:

a) The product obtained after recrystallization from dimethyl formamide still contains the compound (1R,3S, 4R)-3-[(2'-{N,N-dimethylamino}-ethyl)]-1,7,7-tri-[mehyl]-bicyclo[2.2.1]heptane-2-one of Formula V in an amount above the threshold value permitted by Pharmacopoeia (about 0.5%);

b) Dimethyl formamide has a high boiling point and cannot be removed from the product in the required degree because at the high temperature decomposition of the product takes place.

A purification to yield products with a purity sufficient for medicaments according to the Pharmacopoeias could not be attained by known purification processes, such as recrystallization from solvents or fractional distillation. More specifically, by known processes the (1R,2S,4R)-(−)-2-[(2'-{N,N-dimethylamino}-ethoxy)]-2-[phenyl]-1,7,7-tri-[methyl]-bicyclo[2.2.1]heptane of Formula I could not be obtained having no more than 0.2 of (1R,3S,4R)-3-[(2'-{N, N-dimethylamino}-ethyl)]-1,7,7-tri-[methyl]-bicyclo[2.2.1] heptane-2-one of Formula V but only with more than 0.5% of this impurity.

Taking into consideration the severe requirements of Pharmacopoeia, impurities being present in an amount higher than 0.2% by weight may endanger the use of the active principle for pharmaceutical purposes. The impurity (1R,3S,4R)-3-[(2'-{N,N-dimethylamino}-ethyl)]-1,7,7-tri-[methyl]-bicyclo [2.2.1]heptane-2-one of Formula V may therefore cause problems in the use of the compound of Formula I as active principle.

As a summary, it can be stated that when purifying the (1R,2S,4R)-(−)-2-[(2'-{N,N-dimethylamino}-ethoxy)]-2-[phenyl]-1,7,7-tri-[methyl]-bicyclo[2.2.1]heptane of Formula I prepared by the known method, dimethyl formamide would be the only conceivable solvent. However, this recrystallization method is unsuitable for the preparation of a pharmaceutical active ingredient meeting the requirements of the Pharmacopoeias, because dimethyl formamide has such a high boiling point that traces thereof cannot be removed from the product to a sufficient extent. At the high temperature required the compound (1R,2S,4R)-(−)-2-[(2'-{N,N-dimethylamino}-ethoxy)]-2-[phenyl]-1,7,7-tri-[methyl]-bicyclo[2.2.1]heptane of Formula I is subject to decomposition.

As already disclosed above, (+)-camphor of Formula II is present during the alkylation reaction. From (+)-camphor as further contamination (1R,4R)-2-[(2'-{N,N-dimemethylamino}-ethoxy)]1,7,7-tri-[methyl]-bicyclo [2.2.1]heptane of Formula

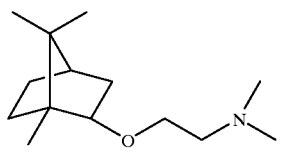

is formed. If an alkali metal hydride or alkali metal amide is used as basic salt forming agent, the amount of the contamination (1R,4R)-2-[(2'-{N,N-dimethylamino}-ethoxy)]-1,7,7-tri-[methyl]-bicyclo[2.2.1]heptane of Formula IV is 1 to 10% by weight. The compound (1R,4R)-2-[(2'-{N,N-dimethylamino}-ethoxy)]-1,7,7tri-[methyl]-bicyclo[2.2.1] heptane of Formula IV has been known from the Prior Art [Yakugaku Zasshi, 75, 1377, (1955); Chem. Abstr. 9340 (1956)]. The compound (1R,4R)-2-[(2'-{N,N-dimethylamino}-ethoxy)]-1,7,7-tri-[methyl]-bicyclo[2.2.1] heptane of Formula IV is formed as follows: the alkali metal hydride or alkali metal amide used for sodium salt formation in the etherification step reduces 1 to 10% of (+)-camphor of Formula II to borneol which is converted under the reaction conditions used into the alkali metal salt and said alkali salt enters with (2-{chloro}-ethyl)-dimethylamine into an alkylation reaction. However, the borneol ether (1R,4R)-2-[(2'-{N,N-dimethylamino}-ethoxy)]-1,7,7-tri-[methyl]-bicyclo[2.2.1]heptane of Formula IV can be separated from the desired compound (1R,2S,4R)-(-)-2-[(2'-[N,N-dimethylamino}-ethoxy)]-2-[phenyl]-1,7,7-tri-[methyl]-bicyclo[2.2.1]heptane of Formula I in the course of working up the reaction mixture.

The problem underlying to the invention is to provide (1R,2S,4R)-(-)-2-[(2'-{N,N-dimethylamino}-ethoxy)]-2-[phenyl]-1,7,7-tri-[methyl]-bicyclo[2.2.1]heptane of Formula I and pharmaceutically acceptable acid addition salts thereof containing amounts of (1R,3S,4R)-3-[(2'-{N,N-dimethylamino}-ethyl)]-1,7,7-tri-[methyl]-bicyclo[2.2.1] heptane-2-one of Formula V small enough to meet the requirements of use for pharmaceutical purposes and a process for preparing such compounds without the necessity of recrystallization purification steps which anyhow would lead only to an insufficient purification and would reduce the yield and moreover would have the drawback that the residual solvent could not be removed from the end product to a sufficient extent even by complicated methods, as well as medicaments containing 1 or more of these compounds and their use.

Surprisingly the above has been solved by the present invention which provides a new product that could not be prepared by the Prior Art.

The present invention is based on the surprising recognition that if the reaction between the reaction mixture containing the compound (1R,2S,4R)-(-)-2-[phenyl]-1,7,7-tri-[methyl]-bicyclo[2.2.1]heptane-2-ol of Formula III and (2-{chloro}-ethyl)-dimethylamine is carried out in the presence of an alkali metal hydride or alkali metal amide in a medium containing dioxane as solvent, the reaction is directed by far in favour of the formation of the desired (1R,2S,4R)-(-)-2-[(2'-{N,N-dimethylamino}-ethoxy)]-2-[phenyl]-1,7,7-tri-[methyl]-bicyclo[2.2.1]heptane of Formula I and the by-product (1R,3S,4R)-3-[(2'-{N,N-dimethylamino}-ethyl)]-1,7,7-tri-[methyl]-bicyclo[2.2.1] heptane-2-one of Formula V is formed only in a minimal amount. The above recognition enables the preparation of the desired compound (1R,2S,4R)-(-)-2-[(2'-{N,N-dimethylamino}-ethoxy)]-2-[phenyl]-1,7,7-tri-[methyl]-bicyclo[2.2.1]heptane of Formula I containing less than 0.2% of compound (1R,3S,4R)-3-[(2'-{N,N-dimethylamino}-ethyl)]-1,7,7-tri-[methyl]-bicyclo[2.2.11]heptane-2-one of Formula V. The compound (1R,2S,4R)-(-)-2-[(2'-{N,N-dimethylamino}-ethoxy)]-2-[phenyl]-1,7,7-tri-[methyl]-bicyclo[2.2.1]heptane of Formula I thus obtained directly meets the requirements of Pharmacopoeia as regards the purity and the content of residual solvent.

In the entire text the percentages regarding the contents of the compounds of Formulae I an V and of other compounds are the result of gas chromatographic analysis they being the ratio of the area under the given peak and the total area under all the peaks.

Hence a subject matter of the invention are (1R,2S,4R-(-)-2-[(2'-{N,N-dimethylamino}-ethoxy)]-2-[phenyl]-1,7,7-tri-[methyl]-bicyclo[2.2.1]heptane of Formula

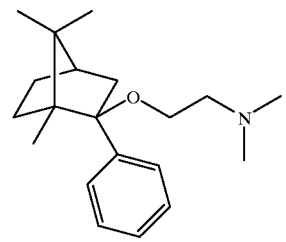

and pharmaceutically acceptable acid addition salts thereof, characterised by that they contain not more than 0.2% of (1R,3S,4R)-3-[(2'-{N,N-dimethylamino}-ethyl)]-1,7,7-tri-[methyl]-bicyclo[2.2.1]heptane-2-one of Formula

V

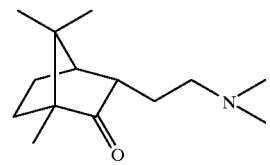

or of a pharmaceutically acceptable acid addition salt thereof.

The term "pharmaceutically acceptable acid addition salts" used in the present patent specification means salts formed with inorganic acids, e.g. hydrochloric acid, hydrobromic acid, sulfuric acid or phosphoric acid, or organic acids, e.g. acetic acid, tartaric acid, succinic acid, malic acid, lactic acid, citric acid, maleic acid or fumaric acid. The salt formed with fumaric acid possesses particularly useful properties.

The (1R,2S,4R)-(-)-2-[(2'-{N,N-dimethylamino}-ethoxy)]-2-[phenyl]-1,7,7-tri-[methyl]-bicyclo[2.2.1] heptane of Formula I has three asymmetrical centres, namely in positions 1, 2, and 4.

According to a preferred embodiment of the invention there is provided for (1R,2S,4R)-(-)-2-[(2'-{N,N-dimethylamino}-ethoxy)]-2-[phenyl]-1,7,7-tri-[methyl-3-bicyclo[2.2.1]heptane fumarate (1:1), characterised by that it contains not more than 0.2% of (1R,3S,4R)-3-[(2'-{N,N-dimethylamino}-ethyl)]-1,7,7-tri-[methyl]-bicyclo[2.2.1] heptane-2-one fumarate (1:1).

Particularly preferably the above (1R,2S,4R)-(-)-2-[(2'-{N,N-dimethylamino}-ethoxy)]-2-[phenyl]-1,7,7-tri-[methyl]-bicyclo[2.2.1]heptane of Formula I and pharmaceutically acceptable acid addition salts thereof according to the invention are characterised by that they contain not more than 0.1%, particularly not more than 0.05%, of the (1R,3S,4R)-3-[(2'-{N,N-dimethylamino}-ethyl)]-1,7,7-tri-[methyl]-bicyclo[2.2.1]heptane-2-one of Formula V or of a pharmaceutically acceptable acid addition salt thereof.

Furthermore particularly preferably the above (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) is characterised by that it contains not more than 0.1%, particularly not more than 0.05%, of the (1R,3S,4R)-3-[(2'-{N,N-dimethylamino}-ethyl)]-1,7,7-tri-[methyl]-bicyclo[2.2.1]heptane-2-one-fumarate (1:1).

Another subject matter of the invention is a process for preparing the (1R,2S,4R)-(−)-2-[(2'-{N,N-dimethylamino}-ethoxy)]-2-[phenyl]-1,7,7-tri-[methyl]-bicyclo[2.2.1]heptane of Formula I and pharmaceutically acceptable acid addition salts thereof according to the invention by converting (+)-1,7,7-tri-[methyl]-bicyclo[2.2.1]heptane-2-one {(+)-camphor} of Formula

II

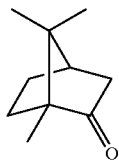

into (1R,2S,4R)-(−)-2-[phenyl]-1,7,7-tri-[methyl]-bicyclo[2.2.1]heptane-2-ol of Formula

III

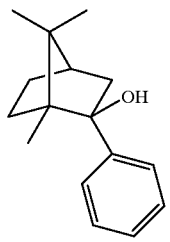

by reacting the former with a metallo-organic compound, if necessary carrying out a decomposition, conveniently hydrolysis, of the reaction product, and reacting the (1R,2S,4R)-(−)-2-[phenyl]-1,7,7-tri-[methyl]-bicyclo[2.2.1]heptane-2-ol of Formula III thus obtained with a (2-{halogeno}-ethyl)-dimethylamine in the presence of a basic salt forming agent in an organic solvent and, if desired, converting the base (1R,2S,4R)-(−)-2-[(2'-{N,N-dimethylamino}-ethoxy)]-2-[phenyl]-1,7,7-tri-[methyl]-bicyclo[2.2.1]heptane of Formula I thus obtained into a salt, characterised by carrying out the reaction of (1R,2S,4R)-(−)-2-[phenyl]-1,7,7-tri-[methyl]-bicyclo[2.2.1]heptane-2-ol of Formula III and (2-{halogeno}-ethyl)-dimethylamine in a medium containing dioxane as a solvent. The invention is not limited to the use of dioxane as the sole solvent but also comprises the use of a solvent containing at least 50% by weight, preferably 75% by weight, of dioxane.

The essential feature of the process of the present invention is that the alkylation is carried out in a solvent which does not favour the alkylation reaction in position 3 of (+)-camphor of Formula II in the presence of a basic salt forming agent. It has been found that dioxane can be used advantageously for this purpose.

Conveniently a phenyl magnesium halide is used as a metallo-organic compound in a Grignard type reaction. Further examples are phenylalkali compounds, such as phenyllithium.

Preferably phenyl magnesium bromide is used. Phenyl magnesium chloride can also be used.

Suitably the process according to the invention may be carried out as follows:

In the first step of the process of the present invention (+)-camphor of Formula II is subjected to Grignard reaction with, for example, phenyl magnesium bromide. The reaction is carried out in a manner known per se. As reaction medium preferably tetrahydrofurane may be used. Phenyl magnesium bromide may be used in an amount of 1 to 3 moles, preferably about 1.5 mole, related to 1 mole of (+)-camphor of Formula II. One may proceed preferably by preparing first the Grignard reagent from magnesium and bromo benzene in the solvent used and thereafter adding the solution of the (+)-camphor of Formula II in an organic solvent at the boiling point of the reaction mixture. It is preferred to use the same solvent for the preparation of the Grignard reagent and the dissolving of the (+)-camphor of Formula II. As a solvent advantageously tetrahydrofurane may be used. Advantageously the reaction is carried out at the boiling point of the reaction mixture.

The reaction mixture is then cooled and the adduct obtained is hydrolysed. Hydrolysis may be carried out in a known manner, preferably in acidic medium. It is preferred to use hydrochloric acid for this purpose.

The (1R,2S,4R)-(−)-2-[phenyl]-1,7,7-tri-[methyl]-bicyclo[2.2.1]heptane-2-ol of Formula III obtained after decomposition of the Grignard complex can be subjected to alkylation without purifying the reaction mixture containing the same. The reaction can be carried out in the presence of unreacted (+)-camphor of Formula II. However, this leads to the formation only of a minor amount of alkylated by-products because according to the process of the present invention the formation of (1R,3S,4R)-3-[(2'-{N,N-dimethylamino}-ethyl)]-1,7,7-tri-[methyl]-bicyclo[2.2.1]heptane-2-one of Formula V is suppressed.

As already mentioned above, alkylation is carried out in a solvent which does not favour the alkylation reaction in position 3 of (+)-camphor of Formula II, i.e. in which (+)-camphor of Formula II is alkylated in position 3 at most only to a very small extent. Dioxane is used as organic solvent because in a medium containing dioxane the alkylation of (+)-camphor of Formula II takes place at most only to a very small extent and consequently the amount of the undesired (1R,3S,4R)-3-[(2'-{N,N-dimethylamino}-ethyl)]-1,7,7-tri-[methyl]-bicyclo[2.2.1]heptane-2-one of Formula V in the end product (1R,2S,4R)-(−)-2-[(2'-{N,N-dimethylamino}-ethoxy)]-2-[phenyl]-1,7,7-tri-[methyl]-bicyclo[2.2.1]heptane of Formula I is not more than 0.2% by weight.

The asymmetrial centres of (1R,2S,4R)-(−)-2-[(2'-{N,N-dimethylamino}-ethoxy)]-2-[phenyl]-1,7,7-tri-[methyl]-bicyclo[2.2.1]heptane of Formula I in positions 1 and 4 are derived from the (+)-1,7,7-tri-[methyl]-bicyclo[2.2.1]heptane-2-one {(+)-camphor} of Formula II.

The alkylation is carried out in the presence of a basic salt forming agent. The term "basic salt forming agent" means basic compounds which convert the hydroxy group into a salt. For this purpose advantageously alkali metal amides, e.g. sodium amide, or alkali metal hydrides, e.g. sodium hydride, may be used. It is preferred to use sodium amide.

Preferably as a (2-{halogeno}-ethyl)-dimethylamine (2-{chloro}-ethyl)-dimethylamine is used.

Suitably the basic salt forming agent is used in an amount of 1 to 3 moles, preferably 1.5 to 2 moles, related to 1 mole of the (1R,2S,4R)-(−)-2-[phenyl]-1,7,7-tri-[methyl]-bicyclo[2.2.1]heptane-2-ol of Formula III. The amount of the alkylating agent is advantageously 1.0 to 2.5 moles, preferably 1 to 1.1 mole, related to the basic salt forming agent. Preferably the alkylation reaction of (1R,2S, 4R)-(−)-2-[phenyl]-1,7,7-tri-[methyl]-bicyclo[2.2.1]heptane-2-ol of Formula III with the (2-{halogeno}-ethyl)-dimethylamine is carried out under heating, particularly at the boiling point of the reaction mixture. Suitably the reaction takes place within about 3 to 5 hours. An advantageous reaction time is about 4 hours.

The (1R,2S,4R)-(−)-2-[(2'-{N,N-dimethylaminol-ethoxy)]-2-[phenyl]-1,7,7-tri-[methyl]-bicyclo[2.2.1]heptane of Formula I may be converted into a pharmaceutically acceptable salt, preferably the fumarate, optionally without isolation of the former. One may preferably proceed as follows: from the reaction mixture obtained after alkylation the inorganic salts are removed by filtration at 0 to 30° C., preferably at 20° C., whereupon the corresponding pharmaceutically acceptable acid, preferably fumaric acid, is added to the filtrate in an approximately equimolar amount (1.0 to 1.5 mole). The crystalline product precipitated from the medium, such as the dioxane medium, is filtered off.

Since the (1R,2S,4R)-(−)-2-[(2'-{N,N-dimethylamino}-ethoxy)-2-[phenyl]-1,7,7-tri-[methyl]-bicyclo[2.2.1]heptane of Formula I or pharmaceutically acceptable acid addition salts thereof, particularly the (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) obtained by the process according to the invention containt[s] in accordance with the requirements of Pharmacopoeia not more than 0.2% of (1R,3S,4R)-3-[(2'-{N,N-dimethylamino}-ethyl)]-1,7,7-tri-[methyl]-bicyclo[2.2.1]heptane-2-one of Formula V or of the pharmaceutically acceptable acid addition salt thereof, respectively, by the process according to the invention recrystallization from dimethyl formamide anyhow leading only to insufficient purification used by known methods has been eliminated, and thus there is no need to remove traces of dimethyl formamide from the pharmaceutically active principle by methods unsuitable for the given purpose, too. Also this latter is a significant progress in view of the impossibility to remove dimethyl formamide to the necessary extent because of its high boiling temperature at which (1R,2S,4R)-(−)-2-[(2'-{N,N-dimethylamino}-ethoxy)]-2-[phenyl]-1,7,7-tri-[methyl]-bicyclo[2.2.1]heptane of Formula I would be decomposed.

The invention also includes compounds of the formula I, and pharmaceutically acceptable acid addition salts thereof, characterized in that they contain not more than 0.2% of the compound of Formula V or of a pharmaceutically acceptable acid addition salt thereof, and also characterized in that they are essentially free of dimethyl formamide. According to an embodiment of the invention, the compounds are completely free of dimethyl formamide. By being "essentially free" of dimethyl formamide, the presence of any minimal amount of dimethyl formamide, if it is present at all, does not limit or preclude the use of the compounds for administration to a host. Compounds that meet Pharmacopoeia limits or U.S. Federal Food and Drug Administration limits on the amount of dimethyl formamide in a compound to be administered to a host are also "essentially free" of dimethyl formamide. Compounds having 0.088% of dimethyl formamide or less by weight, or 880 ppm or less of dimethyl formamide, are also "essentially" free of dimethyl formamide.

The advantage of the process of the present invention is that in addition to providing a highly pure product meeting the strict requirements of Pharmacopoeia it can be carried out with excellent yields. Thus the yield of about 46% shown in the Examples is considerably higher than the yields disclosed in the Prior Art which do not surpass 25% even if (+)-camphor is re-circulated several times.

A further subject matter of the invention are medicaments characterised by that they contain as principle(s) 1 or more compound(s) according to the invention within the above definition, advantageously together with 1 or more in pharmaceutical preparations usual excipient(s).

Preferably the medicaments according to the invention contain (1R,2S,4R)-(−)-2-[(2'-(N,N-dimethylamino}-ethoxy)]-2-[phenyl]-1,7,7-tri-[methyl]-bicyclo[2.2.1]heptane fumarate (1:1) according to the invention within the above definition as an active principle.

Suitably the medicaments according to the invention are in the form of pharmaceutical preparations. They may be prepared by known methods of the pharmaceutical technique. The preparations are preferably suitable for oral administration, e.g. tablets, coated tablets, capsules, solutions, emulsions or suspensions, or for parenteral administration, e.g. intravenous, percutaneous or intramuscular injectable solutions. The compositions may contain usual carriers, e.g. starch, lactose and/or calcium carbonate, and/or water, polyalkylene glycols, sodium chloride solution and/or dextrose solution. The pharmaceutical preparations may also contain usual pharmaceutical auxiliary agents, e.g. emulsifying, stabilising, suspending and/or disintegrating agents, salts to modify the osmotic pressure, buffers and/or antioxidants.

A still further subject matter of the invention is the use of the compounds according to the invention within the above definition for preparing anxiolytic medicaments.

Preferably (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) is used as a compound according to the invention within the above definition.

The invention is further illustrated by the following Examples. The melting points given in the Examples are uncorrected values.

EXAMPLE 1

(1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) [Formula I]

Grignard reaction

To a suspension of 48.6 g (1.5 g atom) magnesium spans and 600 ml of anhydrous tetrahydrofurane a 20 ml portion of a mixture of 236 g (1.5 moles) of bromo benzene and 200 ml of anhydrous tetrahydrofurane is added at the boiling point. Once the Grignard reaction has started, the residual part of the bromo benzene mixture is added to the suspension dropwise within an hour. The reaction mixture is heated to boiling until the magnesium is completely dissolved. To the Grignard compound a solution of 152.2 g (1.0 mole) of (+)-camphor of Formula II and 300 ml of anhydrous tetrahydrofurane is added under constant heating to boiling within about half an hour and the reaction mixture is heated to boiling for a further period of 5 hours.

Hydrolysis

The reaction mixture is cooled to 25° C. and poured onto a mixture of 500 ml of heptane, 400 g of ice, 30 g of sodium chloride and 150 ml of concentrated hydrochloric acid under stirring at 0° C. The organic phase is separated and made alkaline to pH 10 by adding a 25% by weight/volume aqueous ammonium hydroxide solution. After repeated separation the solution is dried and evaporated in vacuo. Thus 220 g of a colourless oil are obtained.

Analysis on the basis of GC
  The test is carried out on a Perkin Elmer Autosystem gas chromatograph.
  Length 10 m (0.25 mm).
  A 14% cyanopropyl 14% methyl polysiloxane fixed phase (CPSil-19CB, Chrompack [Handelsprodukt]) capillary column is used.
  Injection is performed at 200° C.
  Heating speed 10° C./minute.
  Carrier gas: helium.
  Detector: FID, injection temperature 200° C., final temperature 250° C., gas pressure 40 kPa.

(1R,2S,4R)-(−)-2-[phenyl]-1,7,7-tri-[methyl]-bicyclo[2.2.1]heptane-2-ol content: 66.5%

(+)-camphor content: 25%.
Etherification
  To a suspension of 45.5 g (1.05 mole) sodium amide (content: 90% by weight/weight) and 500 ml of anhydrous dioxane a mixture of 220 g of the colourless oil obtained by the hydrolysis containing (1R,2S,4R)-(−)-2-[phenyl]-1,7,7-tri-[methyl]-bicyclo[2.2.1]heptane-2-ol, and 100 ml of anhydrous dioxane is added at the boiling point within half an hour. The mixture is heated to boiling for 2 hours, whereupon 113.0 g (1.05 mole) of (2-{chloro}-ethyl)-dimethylamine are added and the reaction mixture is heated to boiling for a further period of 4 hours.
Formation of the fumarate salt
  The suspension is cooled to 20° C., filtered, to the clear filtrate 121.9 g (1.05 mole) of fumaric acid are added under vigorous stirring. The reaction mixture is heated to boiling for 10 minutes, cooled to 15° C., stirred for a further period of an hour and filtered. The filter cake is washed with dioxane, water and ethanol and dried at 80° C. until free of solvent. Thus 190.5 g (0.456 mole) of white crystals are obtained, yield 45.6% [based on (+)-camphor]. The melting point of the white crystals amounts to 214 to 216° C.
  Analysis for the Formula $C_{20}H_{31}NO·C_4H_4O_4$ (417.55); calculated: C %=69.03%; H %=8.45%; N %=3.35%; found: C %=69.06%; H %=8.42%; N %=3.39%. $[\alpha]_D^{20}=-92.5°$ (c=0.4, dimethyl sulfoxide, 435 nm).
  The product contains less than 0.05% of (1R,3S,4R)-3-[(2'-{N,N-dimethylamino}-ethyl)]-1,7,7-tri-[methyl]-bicyclo[2.2.1]heptane-2-one fumarate (1:1) contamination. 100 g of the 2-(E)-butenedioate salt prepared as described above are stirred in 400 ml of anhydrous ethanol for an hour at 60° C. The suspension is filtered at 10° C. and dried. Thus 97.5 g of the product are obtained. Yield 97.5%.

EXAMPLE 2 (COMPARATIVE EXAMPLE)

(1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) [Formula I]

Reproduction of the Process Disclosed in Hungarian Patent No. 212,574
Grignard Reaction
  To a Grignard compound prepared from 5.52 g (0.23 g atom) of magnesium spans and 36.1 g (0.23 mole) of bromo benzene in 200 ml of anhydrous diethyl ether a solution of 30.4 g (0.20 mole) of (+)-camphor and 50 ml of anhydrous diethyl ether is added. The reaction mixture is heated to boiling for 5 hours. The Grignard complex is decomposed by adding an ice cold aqueous solution of 20 g of ammonium chloride, the mixture is washed three times with 30 ml of water each, separated, dried over anhydrous magnesium sulfate and the solvent is removed by evaporation. Thus 40.5 g of a colourless oil are obtained which contains according to GC

| | |
|---|---|
| 57.5% | of (+) - camphor of Formula II |
| 5.8% | of 1,7,7-tri-[methyl]-bicyclo[2.2.1]heptane-2-ol; (borneol) |
| 34.5% | of (1R,2S,4R)-(−)-2-[phenyl]-1,7,7-tri-[methyl]-bicyclo[2.2.1]heptane-2-ol of Formula III; and |
| 2.2% | of further contaminations in smaller amounts. |

Etherification
  To a suspension of 3.4 g (67 millimoles) of sodium hydride (47.5% by weight/weight dispersion) and 50 ml of anhydrous toluene a solution of 40.0 g of the oil obtained in the Grignard reaction containing (1R,2S,4R)-(−)-2-[phenyl]-1,7,7-tri-[methyl]-bicyclo[2.2.1]heptane-2-ol of Formula III and 30 ml of anhydrous toluene are added. The reaction mixture is heated to boiling for an hour, whereupon a solution of 6.85 g (67 millimoles) of (2-{chloro}-ethyl)-dimethylamine and 10 ml of toluene is added at the boiling point. The reaction mixture is heated to boiling for a further period of 4 hours.
Separation
  The reaction mixture is washed three times with 25 ml of water each. The product is extracted with three equal portions of a solution of 18 g (0.12 mole) of tartaric acid and 40 ml of water. The phases are separated, the aqueous layers are combined, made alkaline to pH 10 with a concentrated ammonium hydroxide solution, extracted three times with 20 ml of dichloro ethane each, dried over magnesium sulfate and the solvent is removed in vacuo. Thus 14.5 g of a colourless oil are obtained which contains according to GC analysis

| | |
|---|---|
| 74.2% | of (1R,2S,4R)-(−)-2-[(2'-{N,N-dimethylamino}-ethoxy)]-2-[phenyl]-1,7,7-tri-[methyl]-bicyclo[2.2.1]heptane of Formula I; |
| 16.5% | of (1R,4R)-2-[(2'-{N,N-dimethylamino}-bicyclo[2.2.1]heptane of Formula IV; |
| 6.5% | of (1R,3S,4R)-3-[(2'-{N,N-dimethylamino}-ethyl)]-1,7,7-tri-[methyl]-bicyclo[2.2.1]heptane-2-one of Formula V; and |
| some % | of further unidentified contaminations each in an amount below 1%. |

Formation of the Fumarate Salt
  To a solution of 14.0 g of the base (1R,2S,4R)-(−)-2-(2'-{N,N-dimethylamino}-ethoxy)]-2-[phenyl]-1,7,7-tri-[methyl]-bicyclo[2.2.1]heptane of Formula I set free from the tartrate salt and 150 ml of ethanol 5.07 g (43.6 millimol) of fumaric acid are added at 70° C. The product is filtered at 0° C. and recrystallized from 50 ml of dimethyl formamide.
  Thus 13.5 g of the desired product (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) of Formula I are obtained in the form of white crystals. Yield 16.2% (based on (+)-camphor]. According to GC analysis in the product 0.5% of (1R,3S,4R)-3-[(2'-{N,N-dimethylamino}-ethyl)]-1,7,7-tri-[methyl]-bicyclo[2.2.1]heptane-2-one of Formula V can be detected. Mp.: 214 to 216° C.
  Analysis for the Formula $C_{20}H_{31}NO·C_4H_4O_4$ (417.55); calculated: C %=69.03%; H %=8.45%; N %=3.35%; found: C %=69.16%; H %=8.52%; N %=3.32%.

What is claimed is:

1. (1R,2S,4R)-(−)-2-[(2'-{N,N-dimethylamino}-ethoxy)]-2-[phenyl]-1,7,7-tri-[methyl]-bicyclo[2.2.1]heptane of Formula

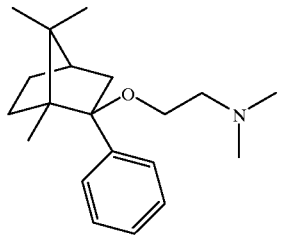

I or a pharmaceutically acceptable acid addition salt thereof, wherein the compound contains not more than 0.2% of (1R,3S,4R)-3-[(2'-{N,N-dimethylamino}-ethyl)]-1,7,7-tri-[methyl]-bicyclo[2.2.1]heptane-2-one of Formula

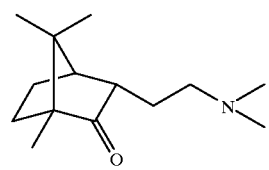

V or of a pharmaceutically acceptable acid addition salt thereof.

2. A compound according to claim 1, wherein the compound is (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1), wherein it contains not more than 0.2% of (1R,3S,4R)-3-[(2'-{N,N-dimethylamino}-methyl)]-1,7,7-tri-[methyl]-bicyclo[2.2.1]heptane-2-one fumarate (1:1).

3. (1R,2S,4R)-(−)-2-[(2'-{N,N-dimethylamino}-ethoxy)]-2-[phenyl]-1,7,7-tri-[methyl]-bicyclo [2.2.1]heptane of Formula I according to claim 1 or a pharmaceutically acceptable acid addition salt thereof, wherein it contains not more than 0.05% of the (1R,3S,4R)-3-[(2'-{N,N-dimethyl-amino}-ethyl)]-1,7,7-tri-[methyl]-bicyclo[2.2.1]heptane-2-one of Formula V or of a pharmaceutically acceptable acid addition salt thereof.

4. A compound according to claim 1, wherein the compound is (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1), wherein it contains not more than 0.05% of (1R,3S,4R)-3-[(2'-{N,N-dimethylamino}-ethyl)]-1,7,7-tri-[methyl]-bicyclo[2.2.1]heptane-2-one fumarate (1:1).

5. A process for preparing the (1R,2S,4R)-(−)-2-[(2'-{N,N-dimethylamino}-ethoxy)]-2-[phenyl]-1,7,7-tri-[methyl]-bicyclo[2.2.1]heptane of Formula I pharmaceutically acceptable acid addition salt thereof according to claim 1 which comprises converting (+)-1,7,7-tri-[methyl]-bicyclo[2.2.1]heptane-2-one {(+)-camphor} of Formula

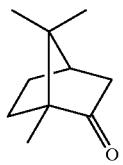

II into (1R,2S,4R)-(−)-2-[phenyl]-1,7,7-tri-[methyl]-bycyclo[2.2.1]heptane-2-ol of Formula

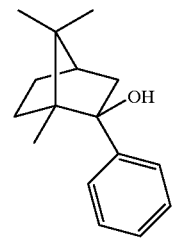

III by reacting the former with a metallo-organic compound, if necessary carrying out a decomposition of the reaction product, and reacting the (1R,2S,4R)-(−)-2-[phenyl]-1,7,7-tri-[methyl]-bicyclo[2.2.1]heptane-2-ol of Formula III thus obtained with a (2-{halogeno}-ethyl)-dimethylamine in the presence of a basic salt forming agent in an organic solvent and, if desired, converting the base (1R,2S,4R)-(−)-2-[(2'-{N,N-dimethylamino}-ethoxy)]-2-[phenyl]-1,7,7-tri-[methyl]-bicyclo[2.2.1]heptane of Formula I thus obtained into a salt, wherein the reaction of (1R,2S,4R)-(−)-2-[phenyl]-1,7,7-tri-[methyl]-bicyclo[2.2.1]heptane-2-ol of Formula III and (2-{halogeno}-ethyl)-dimethylamine is carried out in a medium containing dioxane as solvent.

6. A process according to claim 5, wherein a phenyl magnesium halide is used as the metallo-organic compound in a Grignard type reaction.

7. A process according to claim 5, wherein the metallo-organic compound is phenyl magnesium bromide.

8. A process according to claim 5, wherein the metallo-organic compound is phenyl magnesium chloride.

9. A process according to claim 5, wherein the (2-{halogeno}-ethyl)-dimethylamine is (2-{chloro}-ethyl)-dimethylamine.

10. A process according to claim 5, wherein the basic salt forming agent is sodium amide.

11. A process according to claim 5, wherein the alkylation reaction of (1R,2S,4R)-(−)-2-[phenyl]-1,7,7-tri-[methyl]-bicyclo[2.2.1]heptane-2-ol of Formula III with the (2-{halogeno}-ethyl)-dimethylamine is carried out under heating.

12. A process according to claim 5, wherein the (1R,2S,4R)-(−)-2-[(2'-{N,N-dimethylamino}-ethoxy)]-2-[phenyl]-1,7,7-tri-[methyl]-bicyclo[2.2.1]heptane of Formula I is converted into the fumarate (1:1) without isolation of the former.

13. A pharmaceutical composition, which comprises one or more compounds according to claim 1 together with one or more pharmaceutical excipients.

14. A pharmaceutical composition according to claim 13, which comprises (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) as an active principle, and wherein the (1R,2S,4R)-(−)-2-[(2'-{N,N- dimethylamino}-ethoxy)]-2-[phenyl]-1,7,7-tri-[methyl]-bicyclo[2.2.1]heptane fumarate (1:1) contains not more than 0.2% of (1R,3S,4R)-3-[(2'-{N,N-dimethylamino}-ethyl)]-1,7,7-tri-[methyl]-bicyclo[2.2.1]heptane-2-one fumarate (1:1).

15. A method for treating anxiety in a host, which comprises administering to the host in need of the treatment an effective amount of a compound according to claim 1.

16. A method according to claim 15, which comprises administering (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) to the host, wherein the (1R,2S,4R)-(−)-2-[(2'-{N,N-dimethylamino}-ethoxy)]-2-[phenyl]-1,7,7-tri-[methyl]-bicyclo[2.2.1]heptane fumarate (1:1) contains not more than 0.2% of (1R,3S,4R)-3-[(2'-{N,N-dimethylamino}-ethyl)]-1,7,7-tri-[methyl]-bicyclo[2.2.1]heptane-2-one fumarate (1:1).

17. A process according to claim 5, wherein the alkylation reaction of (1R,2S,4R)-(−)-2-[phenyl]-1,7,7-tri-[methyl]-bicyclo[2.2.1]heptane-2-ol of Formula III with the (2-{halogeno}-ethyl)-dimethylamine is carried out at the boiling point of the reaction mixture.

* * * * *

UNITED STATES PATENT AND TRADEMARK OFFICE
CERTIFICATE OF CORRECTION

PATENT NO.     : 6,335,469 B1
DATED          : January 1, 2002
INVENTOR(S)    : Lukács et al.

It is certified that error appears in the above-identified patent and that said Letters Patent is hereby corrected as shown below:

Title page,
Item [57], delete the ABSTRACT in its entirety and substitute therefor, -- High purity (1R,2S,4R)-(-)-2-[(2'-{N,N-dimethylamino}-ethoxy)]-2-[phenyl]-1,7,7-tri-[methyl]-bicyclo [2.2.1] heptane and pharmaceutically acceptable acid addition salts thereof containing not more than 0.2% of (1R,3S,4R)-3-[(2'-{N,N-dimethylamino}-ethyl)]-1,7,7-tri-[methyl]-bicyclo [2.2.1] heptane-2-one and/or of a pharmaceutically acceptable acid addition salt thereof; a process for the preparation of these compounds; medicaments containing one or more of these compounds, and their use. --

Column 13,
Line 40, "methyl" should read -- ethyl --.
Line 63, "Formula I pharmaceutically" should read -- Formula I or pharmaceutically --.

Signed and Sealed this

Twelfth Day of November, 2002

Attest:

*Attesting Officer*

JAMES E. ROGAN
*Director of the United States Patent and Trademark Office*